(12) United States Patent
Staehle

(10) Patent No.: US 7,120,298 B1
(45) Date of Patent: Oct. 10, 2006

(54) METHOD FOR OBTAINING AND USING MEDICAL DATA

(76) Inventor: Kurt Staehle, 16, Liebenzeller Strasse, D-75242, Neuhausen-Steinegg (DE)

( * ) Notice: Subject to any disclaimer, the term of this patent is extended or adjusted under 35 U.S.C. 154(b) by 978 days.

(21) Appl. No.: 10/218,896

(22) Filed: Aug. 15, 2002

(30) Foreign Application Priority Data

Aug. 16, 2001 (DE) ................................ 101 40 152

(51) Int. Cl.
*G06K 9/00* (2006.01)
*G06K 9/36* (2006.01)
(52) U.S. Cl. ...................... 382/166; 382/165; 382/190; 382/117; 348/229.1
(58) Field of Classification Search ................ 382/162, 382/165–166, 117–118, 115, 128, 190, 199, 382/274, 305; 348/239, 229.1; 351/204; 726/5

See application file for complete search history.

(56) References Cited

U.S. PATENT DOCUMENTS

| 5,291,560 A * | 3/1994 | Daugman | 382/117 |
| 2004/0114782 A1* | 6/2004 | Cho | 382/117 |
| 2005/0019741 A1* | 1/2005 | Kim | 434/365 |
| 2005/0147279 A1* | 7/2005 | Gifford et al. | 382/117 |

FOREIGN PATENT DOCUMENTS

| DE | 3823252 | 1/1989 |
| DE | 3741017 | 3/1995 |
| DE | 198 12 749 A1 | 9/1999 |
| DE | 691 31 681 | 6/2000 |
| EP | 0 487 110 A2 | 5/1992 |
| EP | 0 947 937 A2 | 10/1999 |
| WO | WO 99/67695 A2 | 12/1999 |

OTHER PUBLICATIONS

Carroll, Robert Todd, "Iridology", The Skeptic's Dictionary (Online), http://skepdic.com/iridol.html, 1998.
Williams, Gerald O., "Iris Recognition Technology", IEEE AES Systems Magazine, Apr. 1997, New York, pp. 23-29.

* cited by examiner

*Primary Examiner*—Jingge Wu
*Assistant Examiner*—Ali Bayat
(74) *Attorney, Agent, or Firm*—Browdy and Neimark, PLLC

(57) ABSTRACT

For detecting and statistically securing correlations between the iris of a test subject and his state of health, a data bank with images of the iris of M test subjects is established by means of the following method steps: obtaining an image of the iris (iris chart) of the M test subjects by opto-electronically scanning-in the pixels with defined color values in a predeterminable grid, conversion and storage of the M scanned-in iris charts in M data sets, each with a×b data fields of a value corresponding to the color value of the associated pixel, standardization of the M data sets in such a way that a standard value, which can be predetermined by a rule for computing, is formed for each data field and represents the normal color value of the associated pixel, forming a standard data set (DQ) from the mean values standardized in this way, which constitutes an iris chart with the statistical normal state of the iris of the M test subjects, and storing the standard data set (DQ) in a first section of a data carrier. Standardization permits a statistically unequivocal association (if present) between specific illnesses and corresponding deviations of the iris image from a normal state. This can be used for a computer-controlled iris diagnosis.

5 Claims, 4 Drawing Sheets

NORMAL DATA SET DQ

FIG. 2 AVERAGE DATA SET DQK

METHOD FOR OBTAINING AND USING MEDICAL DATA

FIELD OF THE INVENTION

The invention relates to a method for establishing and evaluating a data bank with images of the irises of M test subjects.

BACKGROUND OF THE INVENTION

It has been known for a long time that the state of the organs of the human and animal body is reflected in areas of the body which are remote from the actual seat of the illness in that changes are caused there, which in turn are available for observation or measurement. The iris represents a typical indicator of this type. The iris is used by iridologists for assessing the state of health of a patient.

OBJECT AND SUMMARY OF THE INVENTION

The object of the invention is the acquisition and statistical securing of correlations between the iris of a test subject and the state of his health.

This object is attained by means of the method disclosed in claim 1. Advantageous further developments are the subject of the dependent claims.

The basic concept of the invention lies in the establishment of a data bank, in which scanned-in images of the irises of test subjects are stored, wherein this storage takes place by means of electronic-optical scanning line by line, for example, something which is known per se in connection with the scanning of photographs, images, or also the scanning of areas of the landscape by means of satellites. Standardization allows a statistically significant assignment (if present) of specific illnesses to corresponding deviations of the iris image from a normal state. This can be used for computer-controlled iris diagnoses.

Thus, an "iris chart" with a defined amount of pixels or data fields is generated, into which the respective scanned-in information from an iris segment regarding brightness and color of this segment is read. A "standard iris chart" can be formed from this.

Besides a total M of test subjects with "normal irises", a number M of test subjects is considered, which have a definite illness characteristic, for example a defined state of an organ, or other health changes which, in accordance with prior experience, can be detected by means of a corresponding modification of one or several segments of the "normal iris".

The iris images of respectively identical segments of the M test subjects are compared with each other by means of a suitable computer program, for example by the employment of suitable filters in data bank programs, with the goal of determining whether a defined change or typical segment structure of the iris, which can extend, for example, over several adjoining segments in a defined shape, coloring or contrast, can be assigned to these M test subjects having a defined organ characteristic. If such a definite association can be found, it is assumed that this specific organ characteristic is reflected in exactly these detected segments or segment structures of the iris. The iris data from these M test subjects are also obtained and combined in a further "standard iris chart".

In a further step, the data sets obtained are edited for further processing in that a "standard form" or normal form of this specific segment combination is formed with a predetermined deviation in respect to spatial extension and/or color arrangement and/or intensity, so that it can be assumed that, when a data set with an iris image of a test subject X with unknown organ characteristics is entered, a repeated segment structure is clearly detected by the processing program containing the said deviations from the "standard form".

By means of the data bank in accordance with the invention, the requirements are met for comparing the iris data of any arbitrary test subject with one or several predetermined iris structure(s) which, in turn, correspond to a defined organ state, as described above, by means of a suitable arrangement consisting of a scanner, computer and computer program.

An apparatus suitable for this, along with the appropriate software, which essentially contains the iris data bank and a suitable selection or filter program, can be operated simply and without substantial previous medical knowledge, since it is necessary to maintain a preset spatial definition, which can be fixed, if required, by appropriate masks or baffles, between the inlet window of the scanner, for example a scanner of the conventional CCD technology, and the eye of the test subject.

A measurement performed as a result permits within a very short time at least a qualitative statement as to whether it is possible to draw conclusions from the total iris structure of the test subject regarding possible states of one or several organs which possibly do not correspond to the normal state.

Once the required software in the form of a data bank has been established, the execution of the method by means of commercially available electronic components, in particular PCs with data bank software, is possible without problems and requires only a small investment.

The individual method steps will now be explained in greater detail, making reference to the drawings.

DETAILED DESCRIPTION OF A PREFERRED EMBODIMENT

Figure 1:
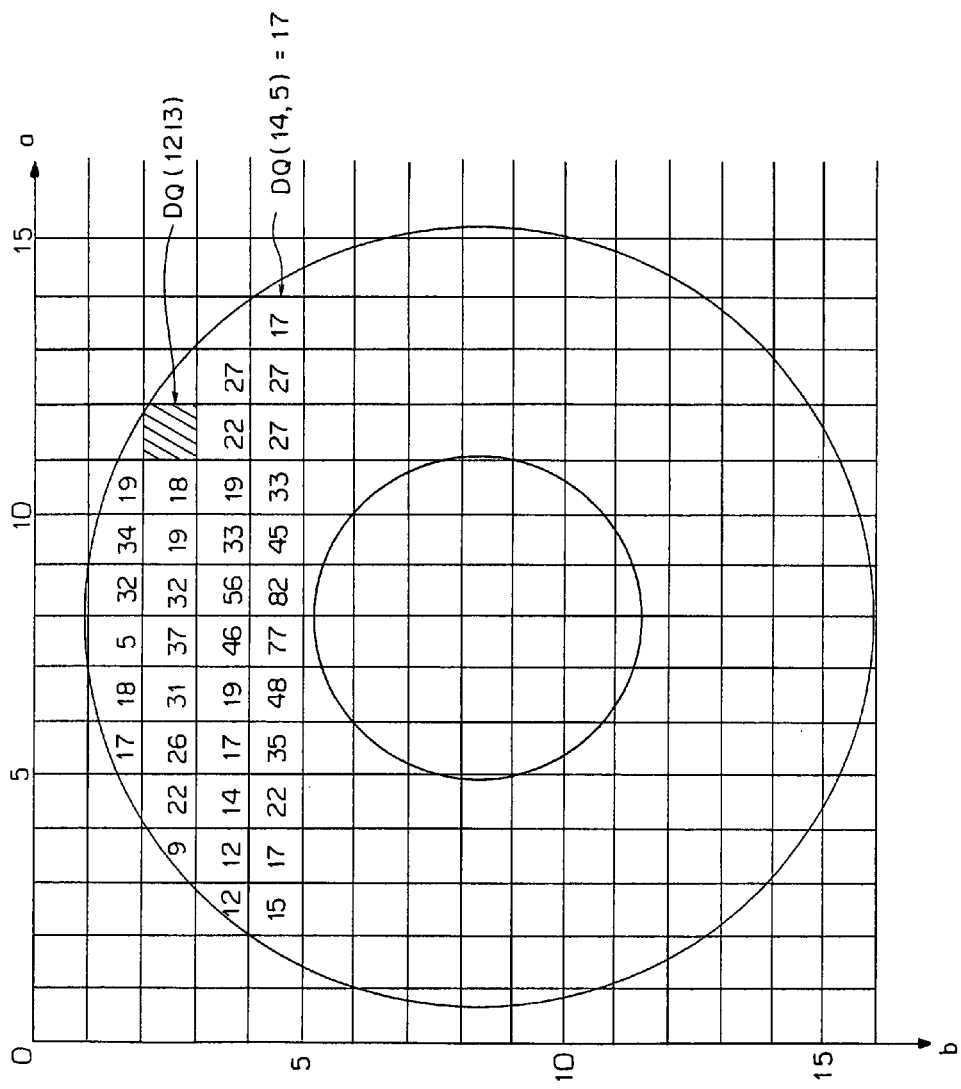
FIG. 1 is a schematic representation of the assignment of pixels to an iris shown as a ring for obtaining a standard data set DQ.
Figure 4:
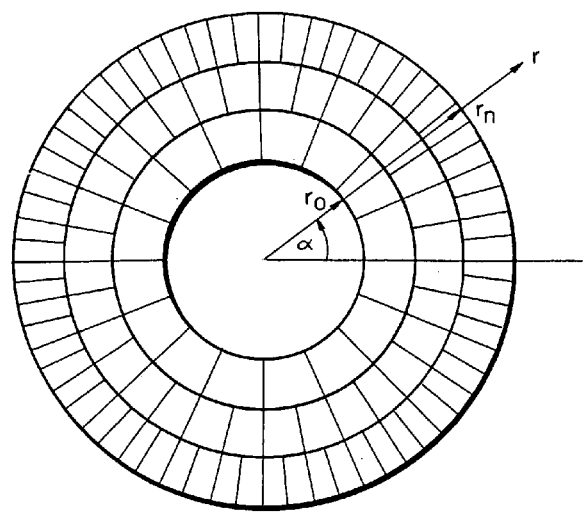
FIG. 4 shows schematic representations of a polar coordinate system for distributing the pixel values.
Figure 4A:
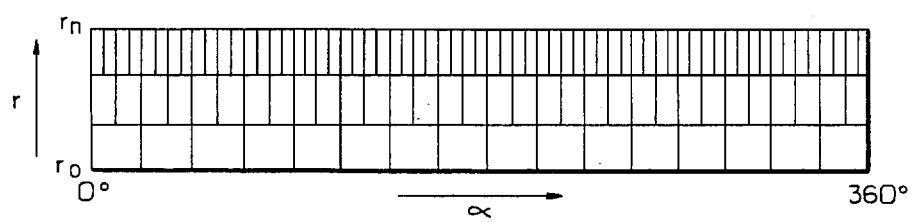

In a schematic representation, FIG. 1 shows an iris of a test subject M, which is represented as a ring (see FIG. 4). For obtaining an image of this iris which can be electronically evaluated ("iris chart"), a pixel grid is placed over this iris, which in the exemplary embodiment represented is limited for reasons of clarity to 16×16 pixels in a Cartesian coordinate system a, b. A corresponding data field is assigned to each optical pixel.

Thus, each square of this grid is intended to represent a pixel with the coordinates a, b with a measured color value which, also for reasons of simplification, is represented as a whole number with values between 0 and 100.

In FIG. 1, the data fields of the standard data set MQ are assigned to "their" pixels. Therefore a data field with the address (12,3) corresponds to the "pixel", shown in hatched lines in FIG. 1, with the coordinates a=12 and b=3. The average measured color value of the data field DQ(14,5) is 17.

With a very much larger number of pixels and a corresponding increase of the depth of color (for example 12 to 24 bits) it is possible in this way to obtain the desired high-resolution iris chart for the left and right iris of a test subject by means of opto-electronic scanning-in.

By means of scanning-in, these pixels are converted into a data set DM, assigned to the test subject M, of respectively a×b data fields, whose value corresponds to the digitized color value of the associated pixel. Therefore the data set DM represents the electronic iris chart of the test subject M.

This process is repeated for all M test subjects, so that a total of M data sets DM are located on a first section of a suitable data carrier, for example the hard disk of a PC.

A data set DQ is computed from these M data sets DM, whose data fields each represent the mean value, or another standard value Q (a, b) of the corresponding data fields of the M data sets DM. Thus, the M data sets DM are standardized in such a way that a standard data set DQ results from the standardized values Q (a,b). This standard data set DQ with the values of the data fields schematically represented in FIG. 1 therefore constitutes the "electronic average iris chart" of the M test subjects. Depending on the value of M (number of test subjects), it is therefore also possible to obtain information regarding the statistical deviation of individual data fields, or pixels, which allows statements as to how far a defined image value, or its associated data field, deviates in a statistically relevant manner from the associated data field of the standard data set MQ.

It is now provided in the further development of the method of the invention to select N test subjects with a specific state of a respective organ K, which deviates from the normal state. The described method is repeated, so that an average data set DQK is created (FIG. 2), which therefore represents a standardized iris chart with a known typical state of the organ K. This organ-specific average data set is stored on a second section of the data carrier.

In a third step it is provided that by means of a linkage of the data fields, in particular the subtraction of the standard data set DQ from the average data set DQK, a difference data set D (Q–QK) is formed (FIG. 3), whose difference data fields δ D (a, b) are formed from the difference of corresponding data fields of the standard data set MQ and the average data set MQK.

Figure 2:
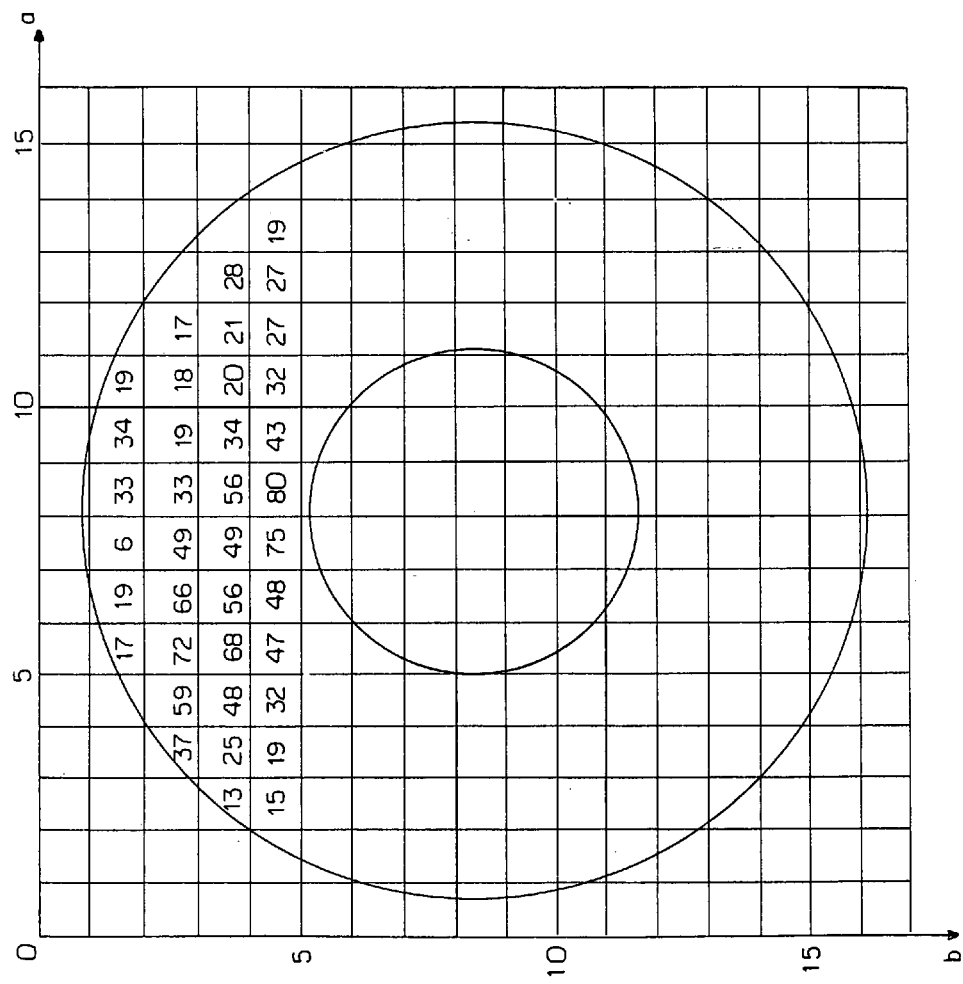
FIG. 2 is a representation corresponding to FIG. 1 with pixel values standardized to average values for obtaining a average data set DQK, which is specific for an organ.
Figure 3:
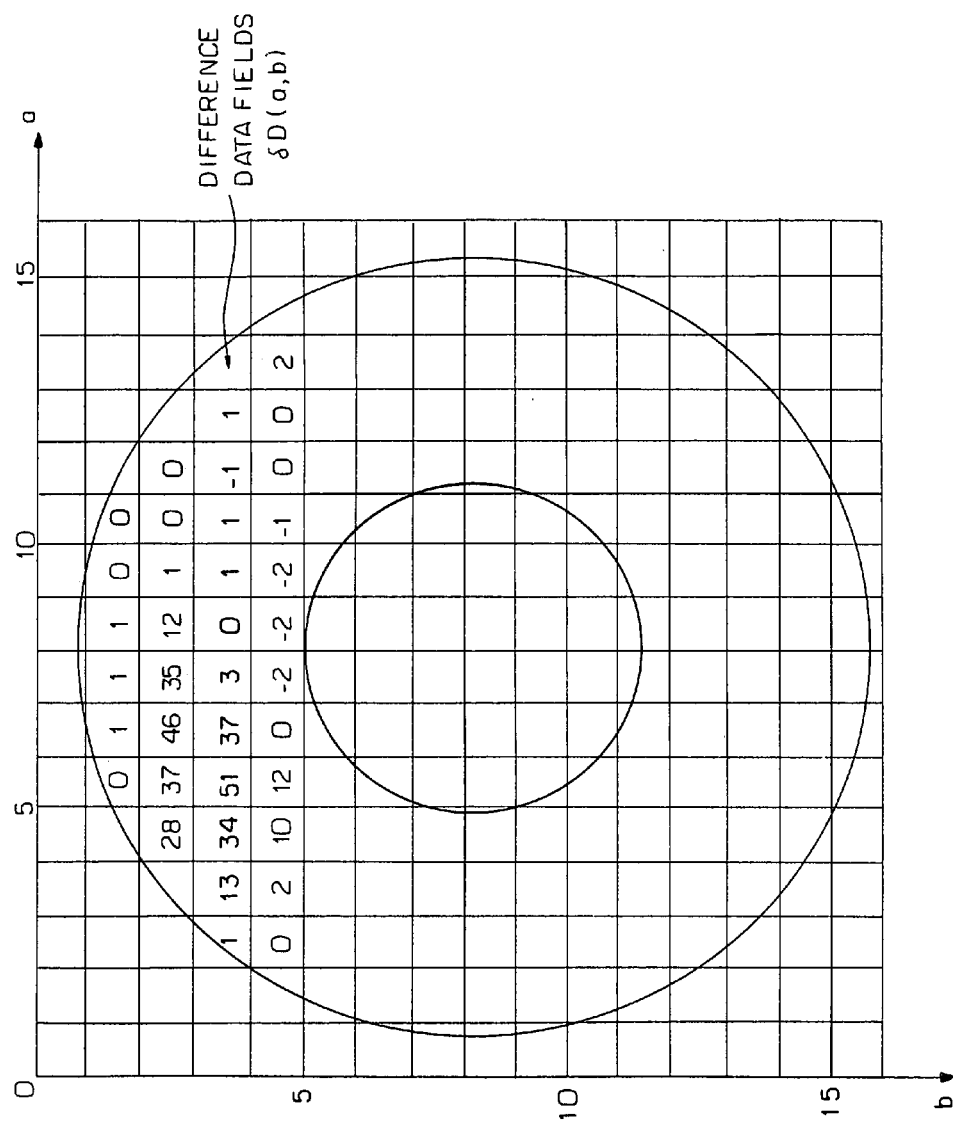
FIG. 3 is a corresponding representation with pixel values which are formed from the difference between the pixel values of the data sets DQ and DQK for obtaining a difference data set M(Q–QK)

From the number example selected in FIGS. 1 to 3 it can be seen that, with a supposed deviation of the state of the organ K from the normal state, the iris shows a significant deviation in the left upper segment or, differently expressed, the associated electronic iris chart has greatly deviating values in this area (corresponding to the color changes in the iris) in comparison with the standard iris chart DQ.

The information from the difference data fields stored on a third section of the data carrier thus shows in which area and to which extent the electronic iris chart DQK typically deviates from the standard iris chart DK in case of a defined state of the organ K.

Thus, information is available from the first to the third section of the data carrier, which assigns typical deviations of the associated iris chart from the standard iris chart to typical organ states which, in connection with a test subject X with an unknown state of one or several organs K, opens the possibility of determining by scanning-in his iris chart and comparing it with the average data set DQK, and/or with the K difference data sets in accordance with FIG. 3 (for each organ K), whether there is an agreement in a statistically significant manner, i.e. whether an organ K of the test subject X is in a state which differs from its normal state, which is represented by a typical change in his iris chart.

This is achieved, for example, in that for corresponding pixels a, b the data sets for the test subject X are successively compared with the difference data sets D(Q–QK), stored in the third section of the data carrier for organs K. This can be signaled when reaching a threshold value, which can be fixed, of the agreement or deviation, from which it is then possible to draw the said conclusions regarding the state of the organ.

In FIGS. 1 to 3, Cartesian coordinates a, b were used for obtaining the pixel grid for the iris chart, however, it is possible in just the same way to provide polar coordinates (τ, α) for this, as schematically indicated in FIG. 4. There, the lower portion represents the developed view of the upper portion.

The polar coordinates have the advantage that they correspond to the circular structure of the iris, so that the spatial assignment of the data fields of the appropriate data sets to the iris chart becomes more graphic. However, this has no effect on the electronic storage and evaluation, since the coordinates can be converted into each other when required and only the structure of the data sets changes, but not their content representing the pixels independently of the format of the data sets.

What is claimed is:

1. A method for establishing and evaluating a data bank with images of the irises of M test subjects, with the following method steps:
   (a) Obtaining an image of the iris (iris chart) of the M test subjects by opto-electronically scanning-in the pixels with defined color values in a predetermined grid;
   (b) Conversion and storage of the M scanned-in iris charts in M data sets, each with a×b data fields of a value corresponding to the color value of the associated pixel;
   (c) Standardization of the M data sets in such a way that a standard value, which can be predetermined by a rule for computing, is formed for each data field and represents the normal color value of the associated pixel;
   (d) Forming a standard data set (DQ) from the mean values standardization in this way, which constitutes an iris chart with the statistical normal state of the iris of the M test subjects;
   (e) Storing the standard data set (DQ) in a first section of a data carrier.

2. The method in accordance with claim 1, characterized in that the method is repeated for N test subjects with a specific state of an organ K which deviates from the normal state, from which respective average data sets DQK result, which show an iris chart with the statistical state of the iris in case of a specific state of a respective organ K, and which are stored in a second section of the data carrier.

3. The method in accordance with claim 2, characterized in that by means of a linkage, in particular the subtraction of corresponding data fields with the same value of a and b of the standard data set (DQ) from the average data set (DQK), a difference data set (D(Q–QK)) is formed for each K, wherein the value of individual or several difference data fields äD (a, b) exceeding a predetermined threshold value S constitutes a statistically significant indicator for a state of a respective organ K which deviates from the normal state, and that the difference data set (D(Q–QK)) is stored in a third section of the data carrier.

4. The method in accordance with claim 3, characterized in that the method is repeated for a test subject X with an unknown state of his organs and is stored on a fourth section of the data carrier.

5. The method in accordance with claim 4, characterized in that corresponding data fields with identical values for a and b of the fourth section of the data carrier are compared with those from at least one of the other sections of the data carrier, and with a predeterminable agreement or deviation the result of the comparison is signaled.

* * * * *